United States Patent [19]

Schneider

[11] Patent Number: 5,596,092

[45] Date of Patent: Jan. 21, 1997

[54] EXTRACTION OF GENOMIC DNA FROM BLOOD USING CATIONIC DETERGENTS

[75] Inventor: Claudio Schneider, Udine, Italy

[73] Assignee: Talent S.r.l., Trieste, Italy

[21] Appl. No.: 268,577

[22] Filed: Jul. 6, 1994

Related U.S. Application Data

[63] Continuation of Ser. No. 783,755, Oct. 28, 1991, abandoned, which is a continuation-in-part of Ser. No. 544,250, Jun. 26, 1990, abandoned.

[51] Int. Cl.$^6$ .................................................... C07H 21/00
[52] U.S. Cl. ...................... 536/25.4; 536/25.41; 564/281
[58] Field of Search .............................. 536/25.41, 25.4; 564/281

[56] References Cited

U.S. PATENT DOCUMENTS

| | | | |
|---|---|---|---|
| 3,176,006 | 3/1965 | Zahn | 260/211.5 |
| 5,010,183 | 4/1991 | MacFarlane | 536/27 |
| 5,300,635 | 4/1994 | MacFarlane | 536/25.4 |
| 5,375,606 | 12/1994 | Slezak et al. | 128/691 |

OTHER PUBLICATIONS

Honig et al., Research in Molecular Biology 3, "Desoxyribonuclein saute–Isolierung", 1974.
Maniatis et al., Molecular Cloning, pp. 9.17–9.19, 9.22–9.23. (1989).
Nucleic Acids Res. 15 (1987) p. 9611, M. Jeanpierre.
Anal. Biochemistry 180 (1989) pp. 276–278 M. B. Johns et al.

*Primary Examiner*—James O. Wilson
*Attorney, Agent, or Firm*—Guido Modiano; Albert Josif

[57] ABSTRACT

A process is disclosed for extracting genomic DNA from a biological sample containing a cell source comprising lysing the biological sample with a first cationic detergent in a solution of high salt concentration greater than 0.5M, under heating at 40° to 80° C., so as to solubilize nucleic acids and proteins present in the cell source. The lysed solution is then extracted with an organic solvent by leaving the DNA in the aqueous phase and precipitating any protein present in the aqueous phase. The DNA is then precipitated from the aqueous solution by diluting it at a salt concentration of below 0.5M and adding thereto a second cationic detergent.

13 Claims, No Drawings

EXTRACTION OF GENOMIC DNA FROM BLOOD USING CATIONIC DETERGENTS

RELATED U.S. APPLICATIONS

This application is a continuation application of application Ser. No. 07/783,755, filed Oct. 28, 1991, now abandoned, which in turn is a continuation-in-part application of application Ser. No. 07/544,250 filed Jun. 26,1990, now abandoned.

BACKGROUND OF THE INVENTION

This invention concerns a method for extracting and purifying genomic DNA from human whole blood a biological cell source, in particular from.

More specifically, the invention provides a method which can be reproduced manually and partly automatically in limited performance times.

The known methods employed for the purification of genomic DNA are complex and time consuming. Routine protocols in current use require at least a crude cell isolation or a nuclei isolation. Moreover, after obtaining the respective "nuclear preparations", most protocols involves long digestions with proteinases, followed by several extractions with phenol. (See for example Molecular Cloning, A Laboratory Manual, Maniatis et al, pg. 9,17–9,18 and Nucl. Acids Res. 3, pg.2303–2306).

Due to the inherent limitations (many careful manipulation of the samples are needed), alternative methods have been developed to optimize the quality and the yield of DNA. These methods are generally based on the use of chaotropic reagents to lyse "nuclear preparations" derived from buffy coats, cells, tissues (See Nucl. Acid Res. 15, 9611, 1987 and Anal. Biochem. 180, 276–278, 1989).

U.S. Pat. No. 5,010,183 discloses purifying DNA and RNA from a biological mixture by simultaneously precipitating them with a cationic detergent.

No references are known to the Applicant disclosing methods that start the preparation from whole blood, thus minimizing the risk of accidental exposure to hazardous viruses during the steps needed to obtain the purified leukocytes or nuclei preparations.

A known "DNA Extractor" apparatus of the Applied Biosystem (Foster City, Calif.), is not satisfactory owing to its low percentage yield and the slowness of the process, based on the chemistry disclosed in Nucleic Acids Res. 3, 2303–2306, 1976: it employs as a reagent phenol, which is expensive, irritant and neurotoxic, and proteinase K, which involves long digestions of the sample and is expensive.

The object of the present applicant is therefore that of providing a method which enables higher percentage yields of pure DNA to be achieved more simply in very short periods of time.

DISCLOSURE OF THE INVENTION

The method to extract and purify genomic DNA is set forth and characterized in the main claim, while the dependent claims describe variants of the idea of the main solution.

The method, according to the invention for the extraction and purification of DNA, starting from human whole blood, comprises at least the following steps:

Lysis of the biological sample, for example of a blood sample, by the addition thereto of a lysis solution containing concentrated first cationic detergents and at least a concentrated salt. Said first cationic detergents are selected preferably from one or more quaternary ammonium salts having a $C_8$–$C_{16}$ alkyl moiety, more preferably from alkyl-trimethylammonium salts, e.g. dodecyltrimethyl-ammonium bromide (DTAB) or tetradecyltrimethylammonium bromide or the respective chlorides (but not alkylbenzyldimethylammonium salts, which have a low solubility in concentrated NaCl) and are present at a concentration for example of 2% –12% usually of 8% The high concentration salt used in the lysis solution can be selected from sodium, potassium and lithium chlorides and bromides, preferably sodium chloride at a concentration above 0.5M, usually from 0.6 to 4M, for example 0.8 to 2M, for example 1M. The volume ratio between blood sample and the lysis solution can range from 1 to 6, for example from 1:2 to 1:3. The joint presence of sodium chloride at a high concentration and of the cationic detergent allows the solubilization of nucleic acids, proteins and membranes. The sample is preferably heated at least for 2' up to 60' to a temperature of 40° to 80° C., for example to 58°–68°° C. to allow the complete denaturation and dissociation of the nuclear proteins bound to solubilized DNA without the use of proteinases or chaotropic agents. The heating step is thus preferable for the complete purification and recovery of DNA. Moreover, the solubilization of nucleic acids in the presence of NaCl of high concentration results in the elimination of most RNAs, which are digested with endogenous ribonucleases activated by the lysis solution of high ionic strength.

Extraction of the sample with an organic solvent, such as dichloromethane, isoamylic alcohol, phenol, but preferably chloroform in a sample/solvent ratio of from 3 to 0.3, preferably of 1. After the addition of chloroform, the cationic detergent and any protein bound thereto, are effectively transferred into the organic phase. Given the efficient removal of the detergent, the remaining proteins are no longer soluble in the aqueous phase containing concentrated sodium chloride. They become "salted out" and are thus precipitated at the interface between organic and aqueous phases. Surprisingly, a single extraction in these conditions of whole blood, tissues and cells, permits a sufficient deproteinization without any further extraction or digestion with proteases.

Thus, the efficient lysis at high temperature, with cationic detergent in a solution of high ionic strength and the efficient removal of the detergent by extraction with chloroform with concomitant efficient protein precipitation in the remaining detergent-free aqueous phase, represent the new synergy at the basis of the present process.

Centrifugation to separate the DNA-containing aqueous phase from the organic phase and from the precipitated protein. Usually the centrifugation is carried out for 2' to 30' at 2000–14,000 g. In the case of whole blood, after the centrifugation step, a proteinaceus clog is formed at the interface between the organic and aqueous phases. Surprisingly, if the organic solvent is chloroform and the detergent is an alkyltrimethylammonium salt, (but not an alkylbenzyldimethylammonium salt or a N-alkylpiridinum salt), the proteinaceus clog is very solid allowing to separate the phases by simply pouring off the upper aqueous phase containing the genomic DNA into a new tube, avoiding pipette aspiration, and maintaining thus the integrity of DNA, increasing its recovery and finally protecting the operator from the exposure to chloroform which is retained at the bottom of the centrifugation tube.

Dilution of the sample in water to decrease the concentration of NaCl below 0.5M and precipitation with a second cationic detergent, preferably a quaternary ammonium salt having a $C_{12}$–$C_{18}$ alkyl moiety, for instance cetyltrimethylammonium bromide or chloride.

Recovery of the genomic DNA. In a first embodiment suited for automation purposes the recovery is carried out by filtration and retention of the genomic DNA on a suitable filter. A preferred filter is a borosilicate sintered glass filter with pores of 10–16 micrometers, e.g. filters Robu Glas (available from Hattert, Germany) with a porosity of 4. Porosities outside this range are either too large to retain the precipitate or too small to permit the flow trough. Glass fiber filters can also be used, but they can release glass particles during the elution step. Polyethylene filters have also been tested, but the final recovery of DNA was rather low.

The filtration is followed by several washes of the DNA on the filter, elution of the genomic DNA and its resuspension in water. The washings are carried out in at least three steps: a first washing step with a low ionic strength aqueous solution, for instance water, to remove the excess of detergent; a second wash, with alcohols and ionic solutions, such as a solution containing sodium chloride, for instance ethanol with a concentration of 50–90% by volume or isopropanol with a concentration of 35–90% by volume both with NaCl 0.05–0.5M; a third wash with alcohol and a low ionic strength solution, such as water, for instance 50–95% ethanol by volume. This sequence of washes with alcoholic-saline solutions allows for an exchange and removal of the detergent and permits to avoid an intermediate step of resuspending the precipitate, before a second precipitation with ethanol, as disclosed in U.S. Pat. No. 5.010.183. After these washings, the filter is dried and finally DNA is eluted by, and resuspended in, a small volume of water, for example 500–1000 microliters; the resulting DNA can be used for the normal applications.

Alternatively, the recovery of DNA after the precipitation with the second cationic detergent, can be made by centrifugation for 2'–30' at 500–2000 g, usually for 5' at 1400 g, whereby a DNA pellet is obtained. The pellet can be resuspended in a high concentration salt solution, for instance NaCl 1M, where the DNA-cationic detergent complex is exchanged to DNA-Na$^+$. DNA can be precipitated again by adding 2 volumes of ethanol and, after a washing of the precipitate with 70% ethanol by volume, DNA can be resuspended in water and can be used for the normal applications.

Percentage yields as compared to the traditional methods vary between 120% and 150%, with a recovery of 40 micrograms per milliliter of blood of a normal donor. The quality of the DNA is extremely satisfactory: the average ratio of the optical readings at 260/280 nm is 1.75–2.0.

DNA obtained in this way can be employed in further analysis, such as in:

1. Enzymatic restriction-Southern blot (J. Mol. Biol. 98,503–517, 1975).
2. Amplification of specific genic fragments with the polymerase chain reaction (PCR) (H. A. Erlich 1989, PCR Technology: principle and applications for DNA amplification, Stokton Press, New York).

As it appears from the above disclosure the method according to the invention uses a new approach of directly and efficaciously solubilizing nucleic acids, proteins and membranes, completely dissociating nuclear proteins from DNA and digesting simultaneously RNAs, by the combined action of cationic detergent, NaCl of high concentration and heating, without need for any long lasting preliminary digestions with proteases. As a consequence also the separation of an aqueous phase containing the desired DNA can be carried in a single extraction step with organic solvent with simultaneous precipitation of proteins, which facilitates their removal.

Accordingly the method according to the invention makes it possible to obtain in about 20 to 30 minutes what can be obtained with the methods known heretofore in about four hours with a lower yield.

Moreover the method according to the invention can be automated, after the step 4 of the process, i.e. precipitation of a DNA-cationic detergent complex, which provides the human genomic DNA in 10–15 minutes.

EXAMPLE 1

Extraction of genomic DNA from whole human blood

The protocol, according to the invention, includes the following main steps:

STEP 1: A sample of whole blood, normally 0.2 to 15 ml, for example 2.5 ml, is subjected to a lysis treatment by adding to it 2 volumes of a concentrated solution of a cationic detergent, for example 8% dodecyltrimethylammonium bromide (DTAB), containing sodium chloride at a concentration of for example 1,5M, EDTA 50 mM and Tris 100 mM, pH 8.7.

This solution is mixed and heated up to 68° C. and let in incubation, for example for five minutes.

STEP 2: the extraction step is carried out by adding 1 volume of chloroform.

STEP 3: the mixture is then subjected to centrifugation with a normal bench centrifuge for some minutes to eliminate the protein portion, for example for about 25' at 2000 g or 15' at 2600 g; superior speeds can be used thus decreasing the centrifugation time. Under these conditions a proteinaceus clog is formed at the interface with the organic phase. In fact, at the ionic conditions used, the detergent goes into the chloroform phase and denatured proteins are "salted out" and thus precipitate at the interface. The aqueous phase is separated by simply pouring it off into a new tube.

STEP 4: after the centrifugation step, the separated aqueous phase is diluted with water in order to decrease its ionic strength below 0,5M NaCl, and a second cationic detergent, for instance, Cetyl-trimethyl-ammonium bromide at a final concentration of 0,1–2% is added thereto. Precipitation of the micellar complex of cationic detergent-DNA takes place after a short mixing operation.

STEP 5: the obtained solution, containing the micellar-DNA complex, can be subjected to filtration. An ultrafiltration can be applied on a filter of sintered borosilicate glass of porosity 4 (pore size between 10 and 16 micron), which retains spread on its surface the DNA-cationic detergent micellar complex in a satisfactory way.

The hydrophilic surface enables DNA to be recovered easily and speedily after the washing operations.

STEP 6: the genomic DNA immobilized on the filter, is first subjected to a series of washings on the filter in order to exchange the detergent-DNA complex, and more specifically:

- a first wash is carried out with an aqueous solution of a low ionic strength to eliminate the excess of detergent for example with water;
- a second wash is carried out with a mixtures of alcohol and an ionic solution, for instance with NaCl 10,2M in 70% ethanol, to exchange the DNA-cationic detergent complex into DNA-Na$^+$.

a third wash is carried out with a mixture of alcohol and a solution of low ionic strength to remove the excess of salts, for instance, 70% ethanol in water.

After having removed traces of alcohol from the filter by blowing a stream of air thereon, the DNA is finally eluted by washing the filter With an aqueous solution of a low ionic strength (water, for instance) at room temperature or under heating, for instance at 68° C.

STEP 5b: Alternatively, the recovery of the precipitated complex of cationic detergent-DNA can be done by centrifugation, for instance for 5' at 1000 g.

DNA is then resolubilized in a solution containing sodium chloride (usually 1.0M), where the exchange of DNA-cationic detergent in DNA-Na$^+$ take place.

To eliminate the cationic detergent, DNA is precipitated again by adding 2 volumes of ethanol and the precipitate is collected after centrifugation at 1000 g for 5'. The pellet is then washed from salts with 70% ethanol, dried and, finally, DNA is resuspended in water.

EXAMPLE 2

Extraction of DNA from cells and tissues.

STEP 1: Cultured cells of eukaryote organisms (such as tumoral cells, connective tissue cells, etc.) and peripheral blood leukocytes are resuspended in phosphate buffer saline (PBS) ($10^7$ cells/ml) and then are lysed by the addition of 2 volumes of a solution containing the cationic detergent DTAB (4–8%), NaCl 1,5M, Tris 100 mM pH 8.7, EDTA 50 mM.

If yeast cells are used, they should be treated with zymoliase in order to digest the cell wall. After this additional step, they can be processed as the other cells.

Tissues are cut and minced in the presence of dry ice or liquid nitrogen. They are then suspended directly into the lysis solution containing NaCl 1M, DTAB (4–8%), Tris 100 mM, pH 8,7, and EDTA 50 mM.

Both tissues and cells are then incubated at 58–68° C. for 5'–30'.

STEP 2: the extraction of DTAB is made by adding 1 volume of chloroform. Before the extraction, the pH of the mixture can be lowered, for instance to 4.5–5, with acetic acid, in order to precipitate the acid polysaccharides after the extraction with chloroform.

STEP 3: the mixture is then subjected to centrifugation with a normal bench centrifuge for some minutes to eliminate the protein portion, for instance for about 25' at 2000 g or 15' at 2600 g. Under these conditions a disk of proteins and polysaccharides is formed at the interface with the organic phase. The disk allows a simplified separation of the viscous aqueous phase by pipetting.

STEP 4: the aqueous phase separated after centrifugation is diluted with water to decrease the ionic strength below 0.5M NaCl, and a second cationic detergent, for instance, Cetyl-trimethyl-ammonium bromide at a final concentration of 0.1–2% is added thereto so that precipitation of the cationic detergent-DNA takes place after a short mixing operation.

STEP 5: the solution containing the micellar complex-DNA is then recovered for example by filtration. A filtration is applied in the same way as in the example n° 1, step 5, whereby the genomic DNA is immobilized on the filter.

STEP 6: the immobilized DNA is subjected to a series of washing on the filter and final elution exactly in the same way as in example 1, step 6.

STEP 5b: Alternatively, the complex of cationic detergent-DNA can be recovered by centrifugation in the same way as for the example n° 1, Step 5b.

I claim:

1. A process for the extraction of genomic DNA from whole blood comprising the steps of:

adding to a whole blood sample a lysis solution comprising a first cationic detergent selected from the group consisting of dodecyltrimethylammonium and tetradecyltrimethylammonium salts, and a salt at a concentration higher than 0.5M, under heating to a temperature of from 40° to 80° C., whereby solubilizing and lysing the nucleic acids and protein contaminants present in the sample of whole blood;

contacting the solution resulting from the previous step with an organic solvent so as to extract therefrom said first cationic detergent and any complex thereof with proteins contained in said sample, while precipitating any protein remaining in the aqueous phase;

centrifuging the mixture resulting from the previous step, whereby separating an organic phase, a solid phase containing the precipitated proteins, and an aqueous phase containing the desired DNA, and separating said aqueous phase from said organic phase and said solid phase;

diluting said aqueous phase with water to a concentration of said salt lower than 0.5M and adding a second detergent whereby precipitating the DNA; and recovering the precipitated DNA.

2. The process of claim 1, wherein said salt is selected from the group consisting of sodium, potassium, lithium chlorides and bromides.

3. The process of claim 1 wherein said salt has a concentration of 0.6 to 4M.

4. The process of claim 1, wherein a volume ratio between said lysis solution and said whole blood sample is ranging from 6 to 1.

5. The process of claim 1, wherein said first cationic detergent is contained in said lysis solution at a concentration of 2 to 12% by weight.

6. The process of claim 1, wherein said first cationic detergent is selected from dodecyltrimethylammonium bromide, and chloride and tetradecyltrimethylammonium bromide and chloride.

7. The process of claim 1, wherein said extraction solvent is selected from chloroform, dichloromethane, isoamylic alcohol and phenol.

8. The process of claim 1, wherein during said centrifugation step the precipitated proteins form a solid clog between said organic and aqueous phase and the separation of these phases is carried out by pouring off the upper phase.

9. The process of claim 1, wherein the second cationic detergent is selected from quaternary ammonium salts having a $C_{12}$–$C_{18}$ alkyl moiety.

10. The process of claim 9, wherein said second cationic detergent is cetyltrimethylammonium bromide.

11. The process of claim 1, wherein the precipitated DNA recovered by filtration or centrifugation.

12. The process of claim 11, wherein said filtration is carried out with a filter made of a material selected from the group consisting of porous sintered borosilicate glass and polyethilene.

13. The process of claim 11, wherein the DNA recovered by filtration is subjected to a series of washings with alcohol and saline solutions comprising at least a first wash with a low ionic strength aqueous solution, a second wash with a mixture of alcohol and ionic solution and a third wash with an alcohol and a solution of low ionic strength.

* * * * *